(12) United States Patent
Chidambaram

(10) Patent No.: US 9,693,966 B2
(45) Date of Patent: *Jul. 4, 2017

(54) GASTRIC REFLUX RESISTANT DOSAGE FORMS

(75) Inventor: Nachiappan Chidambaram, Salt Lake City, UT (US)

(73) Assignee: Banner Life Sciences LLC, High Point, NC (US)

( * ) Notice: Subject to any disclaimer, the term of this patent is extended or adjusted under 35 U.S.C. 154(b) by 1830 days.

This patent is subject to a terminal disclaimer.

(21) Appl. No.: 12/716,593

(22) Filed: Mar. 3, 2010

(65) Prior Publication Data

US 2010/0158958 A1 Jun. 24, 2010

Related U.S. Application Data

(62) Division of application No. 11/316,830, filed on Dec. 22, 2005, now abandoned.

(51) Int. Cl.
| | |
|---|---|
| A61K 9/48 | (2006.01) |
| A61K 9/52 | (2006.01) |
| A61K 35/60 | (2006.01) |
| A61K 47/36 | (2006.01) |
| A61K 47/10 | (2017.01) |
| A61K 47/42 | (2017.01) |

(52) U.S. Cl.
CPC .......... *A61K 9/4825* (2013.01); *A61K 9/4816* (2013.01); *A61K 9/4833* (2013.01); *A61K 35/60* (2013.01); *A61K 47/10* (2013.01); *A61K 47/36* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 4,518,433 A | 5/1985 | McGinley et al. | |
| 4,719,112 A | 1/1988 | Mayer | |
| 4,816,259 A | 3/1989 | Matthews et al. | |
| 5,146,730 A | 9/1992 | Sadek et al. | |
| 5,164,184 A | 11/1992 | Kim | |
| 5,264,223 A | 11/1993 | Yamamoto et al. | |
| 5,330,759 A | 7/1994 | Pagay et al. | |
| 5,431,917 A | 7/1995 | Yamamoto et al. | |
| 5,459,983 A | 10/1995 | Sadek et al. | |
| 5,484,598 A | 1/1996 | Schurig et al. | |
| 5,540,912 A | 7/1996 | Roorda et al. | |
| 5,629,003 A | 5/1997 | Horstmann et al. | |
| 6,482,516 B1 | 11/2002 | Sadek et al. | |
| 2001/0024678 A1 | 9/2001 | Scott et al. | |
| 2001/0036473 A1 | 11/2001 | Scott et al. | |
| 2003/0166508 A1 | 9/2003 | Zhang | |
| 2003/0175335 A1 | 9/2003 | Scott et al. | |
| 2003/0211146 A1 | 11/2003 | Scott et al. | |
| 2004/0037877 A1* | 2/2004 | Opheim | 424/452 |
| 2004/0105835 A1 | 6/2004 | Scott et al. | |
| 2004/0224020 A1 | 11/2004 | Schoenhard | |
| 2004/0265384 A1 | 12/2004 | Scott et al. | |

FOREIGN PATENT DOCUMENTS

| | | |
|---|---|---|
| EP | 0 888 778 | 1/1999 |
| EP | 1 072 633 | 1/2001 |
| EP | 1 132 081 | 9/2001 |
| EP | 1 447 082 | 8/2004 |
| EP | 1 518 552 | 3/2005 |
| JP | 58172313 | 10/1983 |
| JP | 4027352 | 1/1992 |
| JP | 5245366 | 9/1993 |
| JP | 58194810 | 12/1993 |
| WO | 9901115 | 1/1999 |
| WO | WO 00/18835 | 4/2000 |
| WO | WO 01/70385 | 9/2001 |
| WO | WO 03084516 A1 * | 10/2003 |
| WO | WO 2004/030658 | 4/2004 |

OTHER PUBLICATIONS

Allen, et al., "Solid dosage forms and solid modified-release drug delivery system", *Ansel's Pharmaceutical Dosage Forms and Drug Delivery Systems*, 8th Edition:216 (2004).
Demars and Ziegler, "Texture and structure of gelatin/ pectin based gummy confections", *Food Hydrocolloids*, 15:643-653 (2001).
Joseph and Venkatarm, "Indomethacin sustained release from alginate-gelatin or pectin-gelatin coacervates", 126:161-168 (1995).
Annonymous, Gelatin: Pharmaceutical excipients, Handbook of Pharmaceutical Expcipients, URL:http://www.medicinescomplete.com/mc/expicients/current/100193881.htm?q=gelatin&t=search &ss=text&p=1#_hit, retrieved Feb. 4, 2014.
Rowe, et al., "Handbook of pharmaceutical excipients, Pecin" , Handbook of Pharmaceutical Expicients, Pharmaceutical Press, Jan. 1, 2007, pp. 507-508 (2007).
Unknown, Gelling agent & thickeninf agents—Indokemika group , URL:http//www.indokemika-group.com/products/food_ingredients/gelling_agent_thickening_agents/index.html, 1 page, retrieved from the Internet Jan. 30, 2014.

* cited by examiner

*Primary Examiner* — Nissa Westerberg
(74) *Attorney, Agent, or Firm* — Brinks Gilson & Lione

(57) ABSTRACT

Gastric resistant film-forming compositions are described herein. The composition comprises a gastric resistant natural polymer, a film-forming natural polymer, and optionally a gelling agent. Suitable gastric resistant natural polymers include polysaccharides such as pectin and pectin-like polymers. The film-forming composition can be used to prepare soft or hard shell gelatin capsules which can encapsulate a liquid or semi-solid fill material or a solid tablet (Softlet®) comprising an active agent and one or more pharmaceutically acceptable excipients. Alternatively, the composition can be administered as a liquid with an active agent dissolved or dispersed in the composition. The compositions are not only gastric resistant but may also prevent gastric reflux associated with odor causing liquids, such as fish oil or garlic oil, encapsulated in a unit dosage form and esophageal irritation due to the reflux of irritant drugs delivered orally.

28 Claims, No Drawings

GASTRIC REFLUX RESISTANT DOSAGE FORMS

This application is a divisional application of pending prior application U.S. Ser.No. 11/316,830, filed Dec. 22, 2005, entitled "Gastric Reflux Resistant Dosage Forms", by Nachiappan Chidambaram which is herein incorporated in its entirety by reference.

FIELD OF THE INVENTION

The invention is in the field of gastric resistant dosage forms.

BACKGROUND OF THE INVENTION

The use and manufacture of enteric dosage forms are well known in the art. Such dosage forms are described in Remington's Pharmaceutical Sciences, 18$^{th}$ Ed., Mack Publishing Co., Easton, Pa. (1990). Enteric dosage forms are useful for protecting the contents of the dosage form from the gastric conditions of the stomach and/or to protect gastric tissue from an irritant material contained in the dosage form. Enteric dosage forms can also be useful in preventing gastric reflux due to the presence of odor-causing liquids, such as fish oil or garlic oil, in the dosage form.

Enteric-coated dosage forms are typically produced by a film coating process, where a thin film layer of an acid-insoluble (enteric) polymer is applied to the surface of a pre-manufactured dosage form, such as a tablet, and to a lesser extent hard and soft capsules. The enteric coating method involves spraying an aqueous or organic solution or suspension of one or more enteric polymers onto tumbling or moving tablets or capsules, followed by drying at elevated temperatures. Enteric dosage forms made by this coating method can suffer from various process-related problems that affect the performance and/or appearance of the coating. For example, "orange peel" surface formation, also known as surface roughness or mottling, may result. More seriously, coat integrity failure may occur, such as cracking or flaking off of the enteric polymer coating. All coating processes present inherent problems, including possible uneven distribution of the coating ingredients, which can occur under multivariate coating processes.

These problems are common to all enteric dosage forms. However, the problems faced during the coating of gelatin or polysaccharide capsules are even more critical due to the delicate and heat sensitive nature of the soft elastic capsule shell. Both hard and soft capsules can undergo thermally induced agglomeration and distortion of the capsule shell. Moreover, the smoothness and elasticity of the capsule surface makes it difficult to form an intact adhering enteric coating, without a subcoating step to improve the surface of the capsule for coating. Finally, the enteric coatings cause the loss of the normally shiny and clear appearance of gelatin capsule shells, which is a major reason for the popularity and acceptance of gelatin capsules.

Attempts to overcome the limitations associated with coated dosage forms have been made. For example, WO 2004/03068 by Banner Pharmacaps, Inc. ("the '068 application") describes a gel mass that is useful in manufacturing enteric soft or hard shell capsules or enteric tablets without the need for a coating. The gel mass comprises a film-forming, water-soluble polymer, an acid-insoluble polymer and optionally, one or more excipients such as plasticizers, colorants and flavorants. The '068 application, however, discloses the use of synthetic acid-insoluble polymers such as cellulosic polymers and acrylic acid-methacrylic acid copolymers (Eudragit®) which are present in a concentration from 8 to 20% by weight of the wet gel mass.

U.S. Patent Application Publication No. 2003/0175335 by Scott et al, ("the '335 application") describes film forming compositions containing pectin, at least one film-forming polymer, and a setting system for preparing soft and hard shell capsules. The concentration of pectin is 5 to 60% by weight, preferably 10 to 40% by weight. The concentration of the film-forming polymer is 40 to 95% by weight, preferably 50 to 85% by weight. The '335 application discloses a film containing 5 to 25%, preferably 10 to 20% by weight pectin which is suitable to prepare hard shell capsules with enteric properties.

There exists a need for a gastric resistant film-forming composition that contains a gastric resistant natural polymer at relatively lower concentrations.

Therefore, it is an object of the invention to provide a gastric resistant film-forming composition comprising a gastric resistant film-forming composition which comprises a gastric resistant natural polymer at relatively low concentrations and methods of manufacturing thereof.

It is further an object of the invention to provide a gastric resistant capsule shell, which can encapsulate a liquid, semi-solid, or solid fill, which contains a gastric resistant natural polymer at relatively low concentrations and methods of manufacturing thereof.

BRIEF SUMMARY OF THE INVENTION

Gastric resistant film-forming compositions comprise a gastric resistant natural polymer, a film-forming natural polymer, and optionally a gelling agent. The composition can be used for drug delivery either as a liquid or as a gelled capsule. Suitable gastric resistant natural polymers include polysaccharides such as pectin and pectin-like polymers. The concentration of the gastric resistant natural polymer is less than about 5% by weight of the composition, preferably from about 2 to about 4% by weight of the composition. Suitable film-forming natural polymers include gelatin and gelatin-like polymers. The concentration of the film-forming natural polymer is from about 20 to about 40% by weight of the composition, preferably from about 25 to about 40% by weight of the composition. Suitable gelling agents include divalent cations such as $Ca^{2+}$ and $Mg^{2+}$. The concentration of the optional gelling agents is less than about 2% by weight of the composition, preferably less than about 1% by weight of the composition. The composition can further comprise one or more plasticizers to facilitate the film-forming process.

The film-forming composition can be used to prepare soft or hard shell gelatin capsules which can encapsulate a liquid or semi-solid fill material or a solid tablet (Softlet®) comprising an active agent and one or more pharmaceutically acceptable excipients. Alternatively, the composition can be administered as a liquid with an active agent dissolved or dispersed in the composition. The compositions are not only gastric resistant but may also prevent gastric reflux associated with odor causing liquids, such as fish oil or garlic oil, encapsulated in a unit dosage form as well as esophageal irritation due to the reflux of irritant drugs delivered orally.

DETAILED DESCRIPTION OF THE INVENTION

I. Definitions

"Gastric resistant natural polymer" as used herein refers to refers to natural polymers or mixtures of natural polymers which are insoluble in the acidic pH of the stomach.

"Film-forming natural polymer" as used here refers to polymers useful for surface coatings that are applied by spraying, brushing, or various industrial processes, which undergo film formation. In most film-formation processes, a liquid coating of relatively low viscosity is applied to a solid substrate and is cured to a solid, high-molecular-weight, polymer-based adherent film possessing the properties desired by the user. For most common applications, this film has a thickness ranging from 0.5 to 500 micrometers (0.0005 to 0.5 millimeters, or 0.00002 to 0.02 inches).

"Gelling agent" as used herein refers to substances that undergo a high degree of cross-linking or association when hydrated and dispersed in the dispersing medium, or when dissolved in the dispersing medium. This cross-linking or association of the dispersed phase alters the viscosity of the dispersing medium. The movement of the dispersing medium is restricted by the dispersed phase, and the viscosity is increased.

II. Composition

Gastric resistant film-forming compositions comprising (1) a gastric resistant natural polymer; (2) a film-forming natural polymer; and optionally (3) a gelling agent, are described herein.

A. Gastric Resistant Natural Polymers

Exemplary gastric resistant natural polymers include pectin and pectin-like polymers which typically consist mainly of galacturonic acid and galacturonic acid methyl ester units forming linear polysaccharide chains. Typically these polysaccharides are rich in galacturonic acid, rhamnose, arabinose and galactose, for example the polygalacturonans, rhamnogalacturonans and some arabinans, galactans and arabinogalactans. These are normally classified according to the degree of esterification. In high (methyl) ester ("HM") pectin, a relatively high portion of the carboxyl groups occur as methyl esters, and the remaining carboxylic acid groups in the form of the free acid or as its ammonium, potassium, calcium or sodium salts; useful properties may vary with the degree of esterification and with the degree of polymerization. Pectin in which less than 50% of the carboxyl acid units occur as the methyl ester is normally referred to as low (methyl) ester or LM-pectin. In general, low ester pectin is obtained from high ester pectin by a treatment at mild acidic or alkaline conditions. Amidated pectin is obtained from high ester pectin when ammonia is used in the alkaline deesterification process. In this type of pectin some of the remaining carboxylic acid groups have been transformed into the acid amide. The useful properties of amidated pectin may vary with the proportion of ester and amide units and with the degree of polymerization.

In one embodiment, the gastric resistant natural polymer is pectin. The gastric resistant natural polymer is present in an amount less than about 5% by weight of the composition, preferably from about 2 to about 4% by weight of the composition.

B. Film-Forming Natural Polymers

Exemplary film-forming natural polymers include gelatin and gelatin-like polymers. In a preferred embodiment, the film-forming natural polymer is gelatin. A number of other gelatin-like polymers are available commercially. The film-forming natural polymer is present in an amount from about 20 to about 40% by weigh of the composition, preferably from about 25 to about 40% by weight of the composition.

C. Gelling Agent

The composition can optionally contain a gelling agent. Exemplary gelling agents include divalent cations such as $Ca^{2+}$ and $Mg^{2+}$. Source of these ions include inorganic calcium and magnesium salts and calcium gelatin. The gelling agent is present in an amount less than about 2% by weight of the composition, preferably less than about 1% by weight of the composition.

D. Plasticizers

One or more plasticizers can be added to the composition to facilitate the film-forming process. Suitable plasticizers include glycerin, sorbitol, sorbitans, maltitol, glycerol, polyethylene glycol, polyalcohols with 3 to 6 carbon atoms, citric acid, citric acid esters, triethyl citrate and combinations thereof. The concentration of the one or more plasticizers is from about 8% to about 30% by weight of the composition. In one embodiment, the plasticizer is glycerin and/or sorbitol.

III. Method of Making

The film-forming composition can be used to prepare soft or hard shell gelatin capsules which can encapsulate a liquid or semi-solid fill material or a solid tablet (Softlet®) comprising an active agent and one or more pharmaceutically acceptable excipients. Alternatively, the composition can be administered as a liquid with an active agent dissolved or dispersed in the composition.

A. Capsules

1. Shell

The film-forming composition can be used to prepare soft or hard capsules using techniques well known in the art. For example, soft capsules are typically produced using a rotary die encapsulation process. Fill formulations are fed into the encapsulation machine by gravity.

The capsule shell can comprise one or more plasticizers selected from the group consisting of glycerin, sorbitol, sorbitans, maltitol, glycerol, polyethylene glycol, polyalcohols with 3 to 6 carbon atoms, citric acid, citric acid esters, triethyl citrate and combinations thereof.

In addition to the plasticizer(s), the capsule shell can include other suitable shell additives such as opacifiers, colorants, humectants, preservatives, flavorings, and buffering salts and acids.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

2. Fill Material Agents

Soft capsules can used to deliver a wide variety of pharmaceutically active agents. Suitable agents include analgesics, anti-inflammatory agents, antihelmintics, anti-arrhythmic agents, anti-bacterial agents, anti-viral agents, anti-hypertensive agents, anti-coagulants, anti-depressants, anti-diabetics, anti-epileptics, anti-fungal agents, anti-gout agents, anti-malarials, anti-migraine agents, anti muscarinic agents, anti-neoplastic agents, erectile dysfunction improvement agents, immunosupressants, anti-protozoal agents, anti-thyroid agents, anxiolytic agents, sedatives, hypnotics, neuroleptics, -blockers, cardiac inotropic agents, corticosteroids, diuretics, anti-parkinsonian agents, gastro-intestinal agents, histamine $H_1$ and $H_2$ receptor antagonists, keratolytics, lipid regulating agents; anti-anginal agents, nutritional agents, opioid analgesics, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non essential fatty acids, vitamins, minerals and mixtures thereof.

Excipients

Fill formulations may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to surfactants, humectants, plasticizers, crystallization inhibitors, wetting agents, bulk filling agents, solubilizers, bioavailability enhancers, pH adjusting agents, and combinations thereof.

B. Solutions and Suspensions

Alternatively, the composition can be administered as a liquid with an active agent dissolved (e.g. solution) or dispersed (e.g. suspension) in the composition. Suitable active agents are described above. The solution or suspension may be prepared using one or more pharmaceutically acceptable excipients. Suitable excipients include, but are not limited to, surfactants, humectants, plasticizers, crystallization inhibitors, wetting agents, bulk filling agents, solubilizers, bioavailability enhancers, pH adjusting agents, flavorants and combinations thereof.

EXAMPLES

Example 1

Gastric Resistant Dosage Form

The composition of the gastric resistant dosage form is shown below.

| Component | % by weight of the Composition |
| --- | --- |
| Pectin | 4.04 |
| Water | 70.78 |
| Calcium chloride ($CaCl_2$) | 0.05 |
| Gelatin (150 bloom bovine bone) | 17.70 |
| Glycerin | 7.43 |

Example 2

Gastric Resistant Dosage Form

The composition of the gastric resistant dosage form is shown below.

| Component | % by weight of the composition |
| --- | --- |
| Pectin | 4.04 |
| Water | 70.78 |
| Calcium chloride ($CaCl_2$) | 0.05 |
| Gelatin (175 bloom pig skin) | 17.70 |
| Glycerin | 7.43 |

Example 3

Gastric Resistant Dosage Form

The composition of the gastric resistant dosage form is shown below.

| Component | % by weight of the composition |
| --- | --- |
| Pectin | 4.04 |
| Water | 70.71 |
| Calcium chloride ($CaCl_2$) | 0.05 |
| Gelatin (150 bloom bovine bone) | 17.73 |
| Glycerin | 7.43 |

Example 4

Gastric Resistant Dosage Form

The composition of the gastric dosage form is shown below.

| Component | % by weight of the composition |
| --- | --- |
| Pectin | 4.04 |
| Water | 70.71 |
| Calcium chloride ($CaCl_2$) | 0.03 |
| Gelatin (150 bloom bovine bone) | 17.75 |
| Glycerin | 7.43 |

Example 5

Gastric Resistant Dosage Form

The composition of the gastric dosage form is shown below.

| Component | % by weight of the composition |
| --- | --- |
| Pectin | 4.04 |
| Water | 70.71 |
| Calcium chloride ($CaCl_2$) | 0.01 |
| Gelatin (150 bloom bovine bone) | 17.77 |
| Glycerin | 7.43 |

Example 6

Gastric Resistant Dosage Form

The composition of the gastric dosage form is shown below.

| Component | % by weight of the composition |
|---|---|
| Pectin | 4.04 |
| Water | 70.71 |
| Calcium chloride ($CaCl_2$) | 0.007 |
| Gelatin (150 bloom bovine bone) | 17.77 |
| Glycerin | 7.43 |

Example 7

Gastric Resistant Dosage Form

The composition of the gastric dosage form is shown below.

| Component | % by weight of the composition |
|---|---|
| Pectin | 4.04 |
| Water | 68.99 |
| Calcium chloride ($CaCl_2$) | 0.013 |
| Gelatin (150 bloom bovine bone) | 17.79 |
| Glycerin | 9.17 |

Example 8

Gastric Resistant Dosage Form

The composition of the gastric dosage form is shown below.

| Component | % by weight of the composition |
|---|---|
| Pectin | 4.04 |
| Water | 61.89 |
| Calcium chloride ($CaCl_2$) | 0.013 |
| Gelatin (150 bloom bovine bone) | 22.79 |
| Glycerin | 11.27 |

Example 9

Gastric Resistant Dosage Form

The composition of the gastric dosage form is shown below.

| Component | % by weight of the composition |
|---|---|
| Pectin | 4.04 |
| Water | 54.79 |
| Calcium chloride ($CaCl_2$) | 0.013 |
| Gelatin (150 bloom bovine bone) | 27.79 |
| Glycerin | 13.37 |

Example 10

Gastric Resistant Dosage Form

The composition of the gastric dosage form is shown below.

| Component | % by weight of the composition |
|---|---|
| Pectin | 4.04 |
| Water | 47.69 |
| Calcium chloride ($CaCl_2$) | 0.013 |
| Gelatin (150 bloom bovine bone) | 32.79 |
| Glycerin | 15.47 |

Example 11

Gastric Resistant Dosage Form

The composition of the gastric dosage form is shown below.

| Component | % by weight of the composition |
|---|---|
| Pectin | 2.42 |
| Water | 49.11 |
| Calcium chloride ($CaCl_2$) | 0.004 |
| Gelatin (150 bloom bovine bone) | 33.41 |
| Glycerin | 15.05 |

Example 12

Gastric Resistant Dosage Form

The composition of the gastric dosage form is shown below.

| Component | % by weight of the composition |
|---|---|
| Pectin | 2.42 |
| Water | 49.02 |
| Calcium chloride ($CaCl_2$) | 0.008 |
| Gelatin (150 bloom bovine bone) | 33.60 |
| Glycerin | 15.05 |

Example 13

Gastric Resistant Dosage Form

The composition of the gastric dosage form is shown below.

| Component | % by weight of the composition |
|---|---|
| Pectin | 2.42 |
| Water | 49.11 |
| Calcium chloride ($CaCl_2$) | 0.016 |
| Gelatin (150 bloom bovine bone) | 33.41 |
| Glycerin | 15.05 |

Example 14

Gastric Resistant Dosage Form

The composition of the gastric dosage form is shown below.

| Component | % by weight of the composition |
| --- | --- |
| Pectin | 2.42 |
| Water | 49.11 |
| Calcium chloride (CaCl$_2$) | 0.031 |
| Gelatin (150 bloom bovine bone) | 33.39 |
| Glycerin | 15.05 |

Example 15

Gastric Resistant Dosage Form

The composition of the gastric dosage form is shown below.

| Component | % by weight of the composition |
| --- | --- |
| Pectin | 2.50 |
| Water | 47.69 |
| Calcium chloride (CaCl$_2$) | 0.0054 |
| Gelatin (150 bloom bovine bone) | 34.33 |
| Glycerin | 15.47 |

Example 16

Gastric Resistant Dosage Form

The composition of the gastric dosage form is shown below.

| Component | % by weight of the composition |
| --- | --- |
| Pectin | 3.03 |
| Water | 49.11 |
| Calcium chloride (CaCl$_2$) | 0.0049 |
| Gelatin (150 bloom bovine bone) | 32.81 |
| Glycerin | 15.05 |

Example 17

Gastric Resistant Dosage Form

The composition of the gastric dosage form is shown below.

| Component | % by weight of the composition |
| --- | --- |
| Pectin | 3.03 |
| Water | 47.68 |
| Calcium chloride (CaCl$_2$) | 0.0065 |
| Gelatin (150 bloom bovine bone) | 33.81 |
| Glycerin | 15.47 |

Example 18

Gastric Resistant Dosage Form

The composition of the gastric dosage form is shown below.

| Component | % by weight of the composition |
| --- | --- |
| Pectin | 3.03 |
| Water | 49.11 |
| Gelatin (150 bloom bovine bone) | 32.81 |
| Glycerin | 15.05 |

Typical fill materials include, but are not limited to, fish oil, garlic oil, soybean oil, and medium chain triglycerides ("MCT").

Unless defined otherwise, all technical and scientific terms used herein have the same meanings as commonly understood by one of skill in the art to which the disclosed invention belongs. Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. An oral gastric resistant soft capsule shell comprising
   (a) about 2% to about 5% pectin by weight of the capsule shell;
   (b) about 25% to about 40% gelatin by weight of the capsule shell; and
   (c) less than about 2% by weight of the capsule shell of a gelling agent comprising calcium salts, magnesium salts, or calcium gelatin.

2. The shell of claim 1, wherein the gelling agent comprises less than about 1% by weight of the shell.

3. The shell of claim 1, further comprising one or more plasticizers comprising glycerol, sorbitol, sorbitans, maltitol, polyethylene glycol, polyalcohols with 3 to 6 carbon atoms, citric acid, citric acid esters, triethyl citrate, or combinations thereof.

4. The shell of claim 3, wherein the one or more plasticizers comprises from about 8% to about 30% by weight of the shell.

5. The shell of claim 1, further comprising a fill material.

6. The shell of claim 5, wherein the fill material comprises a liquid, semi-solid, or solid.

7. The shell of claim 5, wherein the fill material comprises one or more therapeutic, prophylactic, or diagnostic agents; and optionally one or more pharmaceutically acceptable excipients.

8. The shell of claim 1, wherein the pectin comprises high (methyl) ester pectin.

9. The shell of claim 1, wherein the pectin comprises low (methyl) ester pectin.

10. The shell of claim 1, wherein the pectin comprises amidated pectin.

11. The shell of claim 5, wherein the fill material comprises fish oil.

12. An oral gastric resistant dosage form comprising a soft capsule shell comprising
    (a) about 2% to about 5% pectin by weight of the capsule shell;

(b) about 25% to about 40% gelatin by weight of the capsule shell; and
(c) less than about 2% by weight of the capsule shell of a gelling agent comprising calcium salts, magnesium salts, or calcium gelatin;
(d) about 8% to about 30% by weight of the capsule shell of a plasticizer comprising glycerol, sorbitol, or a combination thereof; and
a fill comprising a pharmaceutically active agent or a nutritional, and optionally one or more pharmaceutically acceptable excipients.

13. An oral gastric resistant dosage form comprising a soft capsule shell encapsulating a fill, the shell comprising
(a) about 2% to about 5% pectin by weight of the capsule shell;
(b) about 25% to about 40% gelatin by weight of the capsule shell; and
(c) less than about 2% by weight of the capsule shell of a gelling agent comprising calcium salts, and
(d) about 8% to about 30% by weight of the capsule shell of a plasticizer comprising glycerol; and
a fill comprising fish oil.

14. The shell of claim 3, wherein the plasticizer comprises glycerol.

15. The shell of claim 1, further comprising glycerol in an amount of about 8% to about 30% by weight of the capsule shell.

16. The shell of claim 1, further comprising water.

17. The shell of claim 1, wherein pectin comprises about 3% by weight of the capsule shell.

18. The shell of claim 1, wherein the gelling agent comprises a calcium salt.

19. The shell of claim 1, wherein the gelling agent comprises about 0.01% by weight of the capsule shell.

20. The dosage form of claim 12, wherein the plasticizer comprises glycerol.

21. The dosage form of claim 12, wherein the shell further comprises water.

22. The dosage form of claim 12, wherein pectin comprises about 3% by weight of the capsule shell.

23. The dosage form of claim 12, wherein the gelling agent comprises a calcium salt.

24. The dosage form of claim 12, wherein the gelling agent comprises about 0.01% by weight of the capsule shell.

25. The dosage form of claim 12, wherein the fill comprises fish oil.

26. The dosage form of claim 13, wherein the shell further comprises water.

27. The dosage form of claim 13, wherein pectin comprises about 3% by weight of the capsule shell.

28. The dosage form of claim 13, wherein the gelling agent comprises about 0.01% by weight of the capsule shell.

* * * * *